(12) United States Patent
Martinewski (10) Patent No.: US 10,935,530 B2
(45) Date of Patent: Mar. 2, 2021

(54) ANALYSIS UNIT FOR REMOVABLE INSTALLATION OF A GAS MEASUREMENT DEVICE

(71) Applicant: AVL EMISSION TEST SYSTEMS GMBH, Neuss (DE)

(72) Inventor: Georg Martinewski, Duesseldorf (DE)

(73) Assignee: AVL EMISSION TEST SYSTEMS GMBH, Neuss (DE)

(*) Notice: Subject to any disclaimer, the term of this patent is extended or adjusted under 35 U.S.C. 154(b) by 18 days.

(21) Appl. No.: 16/462,939

(22) PCT Filed: Nov. 20, 2017

(86) PCT No.: PCT/EP2017/079759
§ 371 (c)(1),
(2) Date: May 22, 2019

(87) PCT Pub. No.: WO2018/104037
PCT Pub. Date: Jun. 14, 2018

(65) Prior Publication Data
US 2020/0064320 A1 Feb. 27, 2020

(30) Foreign Application Priority Data
Dec. 9, 2016 (DE) .......................... 10 2016 123 925

(51) Int. Cl.
*G01N 33/00* (2006.01)
*G01N 27/62* (2006.01)
(52) U.S. Cl.
CPC ......... *G01N 33/0011* (2013.01); *G01N 27/62* (2013.01)
(58) Field of Classification Search
CPC ............................ G01N 33/0011; G01N 27/62
See application file for complete search history.

(56) References Cited

U.S. PATENT DOCUMENTS 5,852,227 A 12/1998 Garthe
6,148,613 A 11/2000 Klopp et al.
(Continued)

FOREIGN PATENT DOCUMENTS

DE 24 54 285 C3 5/1976
DE 196 21 293 A1 11/1997
(Continued)

OTHER PUBLICATIONS

ACX Advanced CGA Solutions Data Sheet: "ACX Analyzer Systems for Emission Monitoring, Cement Applications and Process Measurement", http://www.cemsi.on.ca/Files/ACX_data.pdf, pp. 1-24 (May 2007, retrieved on Mar. 14, 2013).
(Continued)

*Primary Examiner* — Reena Aurora
(74) *Attorney, Agent, or Firm* — Norman B. Thot (57) ABSTRACT

An analysis unit includes a frontal plane to access the analysis unit, a mounting plane perpendicular to the frontal plane, and a gas measurement device. The gas measurement device includes a connection housing part and a main housing part. The connection housing part includes an inlet channel and an outlet channel which extend from the mounting plane to a first connection plane. The main housing part includes a second connection plane which corresponds to the first connection plane. The main housing part rests on the first connection plane. The main housing part further includes an inflow channel which fluidically communicates with the inlet channel via the first connection plane, and a recirculation channel which fluidically communicates with the outlet channel via the first connection plane. The first and second connection planes are tilted at an angle of 45° from the mounting plane in a direction of the frontal plane.

14 Claims, 4 Drawing Sheets

(56) References Cited

U.S. PATENT DOCUMENTS

| | | | |
|---|---|---|---|
| 6,282,944 B1 * | 9/2001 | Bornemann | G01N 1/2252 |
| | | | 73/114.71 |
| 10,054,574 B2 * | 8/2018 | Hansmann | G01N 31/222 |
| 2006/0207426 A1 | 9/2006 | Platt et al. | |
| 2010/0303674 A1 | 12/2010 | Sutherland et al. | |

FOREIGN PATENT DOCUMENTS

| | | |
|---|---|---|
| DE | 10 2008 060 914 A1 | 6/2009 |
| DE | 20 2009 014 666 U1 | 4/2010 |
| EP | 2 437 881 B1 | 8/2013 |
| WO | WO 2006/102094 A2 | 9/2006 |

OTHER PUBLICATIONS

Siemens AG: "Analytical Application Sets", Siemens PA 01.2015, http://www.automation.siemens.com/sc-static/catalogs/catalog/pa/PA01/en/PA01_en_Kap04.pdf, pp. 1-70 (retrieved on Jan. 27, 2016).

Gasmet Technologies Oy: "Gasmet Engine Emissions Monitoring System EEMS", technical data, http://ansyco.de/images/tiedostot/product-downloads/gasmet_eems_technical_data_v1.4.pdf, pp. 1-2 (Jan. 13, 2014).

Sick Product Information: "GMS800 Fidor Total Hydrocarbon Analyzer", Continuous Monitoring of Hydrocarbon Emissions, https://www.sick.com/media/dox/0/20/320/Product_information_GMS800_FIDOR_Total_Hydrocarbon_Analyzer_en_IM0044320.PDF, pp. 1-12 (Sep. 3, 2013).

* cited by examiner

ANALYSIS UNIT FOR REMOVABLE INSTALLATION OF A GAS MEASUREMENT DEVICE

CROSS REFERENCE TO PRIOR APPLICATIONS

This application is a U.S. National Phase application under 35 U.S.C. § 371 of International Application No. PCT/EP2017/079759, filed on Nov. 20, 2017 and which claims benefit to German Patent Application No. 10 2016 123 925.9, filed on Dec. 9, 2016. The International Application was published in German on Jun. 14, 2018 as WO 2018/104037 A1 under PCT Article 21(2).

FIELD

The present invention relates to an analysis unit with a frontal plane, from which the analysis unit is accessible, parallel mounting planes, which are arranged perpendicular to the frontal plane, a gas measurement device, which has at least one connection housing part, through which an inlet channel extends from the mounting plane to a connection plane and through which an outlet channel extends from the connection plane to the mounting plane, and a main housing part with a connection plane that corresponds to the connection plane of the connection housing part and on which the main housing part rests against the connection housing part, wherein the main housing part is equipped with an inflow channel, which is in fluid communication with the inlet channel of the connection housing part via the connection plane, and a recirculation channel which is in fluid communication with the outlet channel of the connection housing part via the connection plane.

BACKGROUND

Such analysis units are usually arranged in control cabinets that have a door on their front side which allows the technician or the operating personnel to access the individual measurement devices and their peripheral elements so that these are if possible mounted so as to be accessible from the front side. The measurement devices and peripheral elements usually comprise several housing parts of which at least one is mounted, for example, on one of the cabinet floors, which is then used as a mounting plane, while all other housing parts are mounted thereon. Access to individual devices may be restricted depending on the available installation space so that installation and removal is difficult, in particular if tools are used.

The flame ionization detector described, for example, in DE 196 21 293 A1, comprises, in addition to the space in which the flame or the flames are produced, the gas and the power line leading to the space for supplying the electrodes, the elements to determine the electrons released during ionization, and the connected electric evaluation unit, a converter in which hydrocarbon molecules, except methane, are converted with hydrogen molecules and oxygen molecules on a catalyst surface to carbon dioxide and water. In order to determine the hydrogen molecules, the exhaust gas flow flows through a flame of the flame ionization detector, while exhaust gas flow that passes the converter flows through the other flame, so that only the proportion of methane in the exhaust gas is determined at the other flame, wherein the conversion rate of the converter must be taken into account, which is approximately 13% for methane. The amount of hydrocarbons without methane can then be determined by subtraction. Although these components are assembled to a flame ionization detector, they comprise different housing parts to ensure that they are installed correctly and that individual components of the flame ionization detector, such as the catalysts of the converter, can be accessed in case of a malfunction without having to completely remove the flame ionization detector.

A disadvantage of the known systems is that the installation of the measurement devices or the housing parts of the devices is always fixed regardless of the available installation space. The accessibility is also often difficult, thereby significantly increasing installation and maintenance times.

SUMMARY

An aspect of the present invention is to provide an analysis unit where the measurement devices and/or the peripheral devices can be easily installed and removed by improving the accessibility of these devices while at the same time adapting the installation direction to the installation space without having to change the housing parts.

In an embodiment, the present invention provides an analysis unit which includes a frontal plane from which the analysis unit is accessible, mounting planes each, of which are arranged parallel with each other and perpendicular to the frontal plane, and a gas measurement device. The gas measurement device comprises at least one connection housing part and a main housing part. The at least one connection housing part comprises an inlet channel which is arranged to extend from one of the mounting planes to a first connection plane, and an outlet channel which is arranged to extend from the first connection plane to the one of the mounting planes. The main housing part comprises a second connection plane which corresponds to the first connection plane of the at least one connection housing part. The main housing part is arranged to rest on the first connection plane of the at least one connection housing part. The main housing part further comprises an inflow channel which is arranged to be in a fluid communication with the inlet channel of the at least one connection housing part via the first connection plane, and a recirculation channel which is arranged to be in a fluid communication with the outlet channel of the connection housing part via the first connection plane. The first connection plane and the second connection plane are each are tilted at an angle of 45° from the one of the mounting planes in a direction of the frontal plane.

BRIEF DESCRIPTION OF THE DRAWINGS

The present invention is described in greater detail below on the basis of embodiments and of the drawings in which.

DETAILED DESCRIPTION

The present invention provides that a flange connecting the two housing parts remains easily accessible from the front side because the corresponding connection planes are tilted at an angle of 45° from the mounting plane in a direction of the frontal plane. Especially in the front area there is space for using tools, such as a wrench. If the gas leading channels are correctly arranged, the main housing can also be placed and mounted on the connection housing part in two directions by rotating the main housing part around its own axis and tilting it by 90°. Two extension directions of the main housing part, placed at an angle of 90° towards each other, can thus be created during installation, whereby mounting is possible depending on the available installation space.

All bores, channels, receiving openings or recesses in the connection housing part and in the main housing part can, for example, be arranged symmetrically relative to a symmetry plane running perpendicular to the mounting plane. A correct gas flow is thereby provided for both alternative installation directions without having to adapt the components that will be mounted to each other.

It is further advantageous if the main housing part comprises a flange plate whose first flange face forms the connection plane and whose second flange face runs parallel to the connection plane, wherein bores extend from the first flange face to the second flange face through the flange plate. The insertion direction of the screws and thus the direction of the force used for mounting with the screws is always directed at an angle of 45° towards the extension direction of the housing part regardless of the mounting direction of the main housing part. The flange face and the screw heads for mounting are thus always easily accessible from the front side.

In order to provide a particularly simple mounting by tightening the screws, an embodiment of the present invention provides that the connection housing part can, for example, be equipped with two threaded holes, wherein screws can be tightened into the threaded holes, which then extend through the bores of the flange plate into the threaded holes.

It is further advantageous if a body of the main housing part extends between the two bores at an angle of 45° relative to the flange faces, wherein the main housing part can be mounted in two perpendicularly arranged positions on the connection housing part. The main housing part thus extends in the cabinet either perpendicular to the mounting plane or to the cabinet floor or to the front side. Depending on the available installation space or the control cabinet used, an installation with common parts can be carried out in this way, thereby reducing production costs.

In an embodiment of the present invention, the inclined connection plane of the connection housing part can, for example, merge into a contact face, which is arranged parallel to the mounting plane. The inclined connection plane of the main housing part correspondingly merges into a face which is angled by 45° relative to the connection plane and which can be placed on the contact face of the connection housing part in a first mounting position. This simplifies the installation process since the main housing part can be placed on the connection housing part during installation without having to be held. The inclined connection plane nonetheless remains to improve accessibility.

In an embodiment of the present invention, converter material for converting hydrocarbons into methane can, for example, be arranged in the inflow channel and/or in the recirculation channel of the main housing part. The main housing part correspondingly serves as a housing of a converter, which main housing part can be easily installed and whose accessibility for exchanging the converter material is maintained without having to remove the entire flame ionization detector. Because the converter material is arranged in two parallel channels, the length of a cylinder can be reduced, and the required volume for converting can thus be provided in a small installation space.

This reduction, especially of the axial overall length of a converter, can be reduced even further due to the fact that two further parallel flow channels are formed in the main housing part between the inflow channel and the recirculation channel in which converter material is arranged and which are connected to each other with the respective adjacent inflow channel or recirculation channel via axial recesses between the ending of the inflow channel facing away from the connection housing part and the adjacent flow channel and the recirculation channel and the adjacent flow channel.

A complete through-flow of all four gas channels with converter material is provided by a connection channel in the main housing part at the ending facing to the connection housing part between the two flow channels so that the main housing part is flowed through in a meandering way. The converter channels are correspondingly flowed through consecutively without leaving the main housing part.

The connection plane of the connection housing part can, for example, be equipped with a first circular recess into which the inlet channel leads and which is in fluid communication with the inflow channel of the main housing part, and with a second circular recess into which the at least one recirculation channel of the main housing part leads and which is in fluid communication with the outlet channel of the connection housing part, and with an oblong recess into which the two flow channels of the main housing part lead. The gas flow is thereby extended to the entire cross-section of the channels comprising the converter material before reaching the converter material in the channels of the main housing part so that an optimum flow is achieved herein. An increased pressure loss is also avoided by uniform available cross-sections.

In an embodiment of the present invention, the inflow channel, the recirculation channel, and the two flow channels can, for example, be closed with a plate screwed on their ending opposite to the connection housing part. This makes it easier to create the main housing part into which the channels can be inserted by a simple boring or milling, and thus also to access and fill the channels with the converter material.

It can also be advantageous if the main housing part is equipped with at least one first receiving opening in which a heating cartridge is arranged and in which at least one second receiving opening is formed in which a temperature sensor is arranged. A temperature of, for example, approximately 280° C. can thereby be produced and controlled in the converter in order to provide an optimum conversion of the hydrocarbons.

The gas measurement device can, for example, be a flame ionization detector, and the main housing part can correspondingly form a converter. This gas measurement device is usually made up of different housing parts whose accessibility must be provided as individually as possible in order to be able to carry out maintenance.

An analysis unit is thus provided that is easy to maintain and to install due to significantly improved accessibility. Production advantages are also achieved due to the two mounting directions, since optimum installation directions with common parts can also be realized for different available installation spaces. Special advantages are achieved in terms of creating, installing and maintaining a converter of a flame ionization detector.

An exemplary embodiment of an analysis unit according to the present invention is shown in the drawings and is described below.

Figure 1:
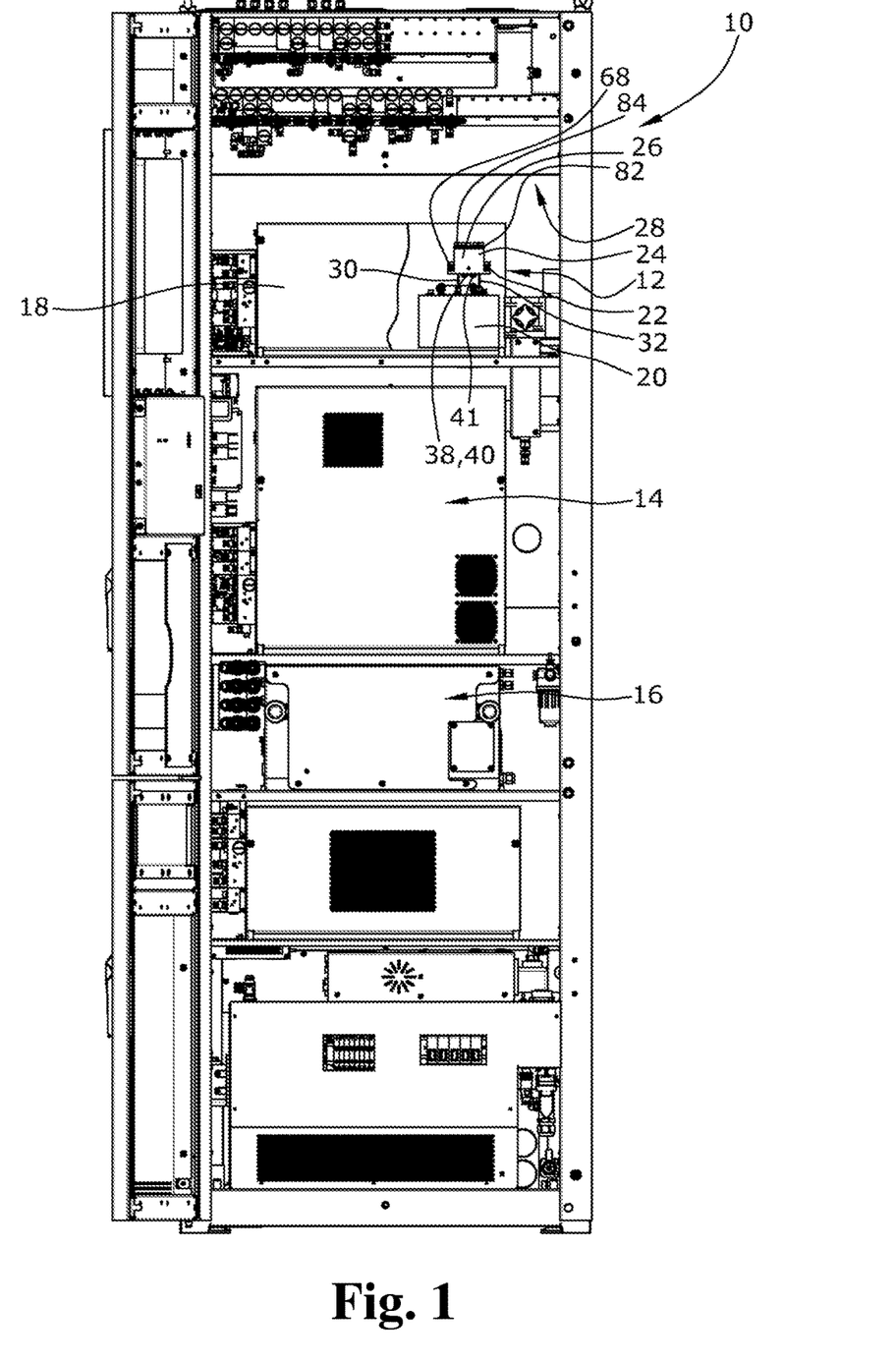
FIG. 1 shows a section of a control cabinet with an analysis unit according to the present invention.

The analysis unit is arranged as a control cabinet 10 that comprises various gas measurement devices 12, 14, 16. The top of these gas measurement devices 12 is a flame ionization detector in whose exterior housing 18 several more housing parts 20, 22, 24 are arranged, which have to be mounted. Several assembled housing parts 20 surround the space equipped with two flames of the flame ionization detector 12, with the required gas inlet line and gas outlet line and with the required electronics for measuring and evaluating at the flame ionization detector. A proportion of methane and a proportion of the overall existing hydrocarbons is determined via the two flames in a known manner by conveying the measuring gas with a carrier gas flow, containing, among other things, hydrogen, to the flame, where a thermic ionization takes places, which creates a measurable conductivity between two electrodes, which is a reference for the hydrocarbons contained in the measuring gas.

The measuring gas flow is, however, divided into a first partial flow, which is directly conveyed to the first flame, so that a gas flow of all existing hydrocarbons can be determined, and a second partial flow that is conveyed to a second flame via a converter 26. All hydrocarbons, except methane, are converted, in the presence of hydrogen and oxygen, in the converter 26 on a converter material, which can, for example, be hopcalite, a mixture of copper oxide and manganese oxide, to carbon dioxide and water. While the remaining hydrocarbons are almost completely converted, methane is only converted in the converter 26 by 13%, so that the proportion of methane in the total hydrocarbons present can be determined by correspondingly converting the determined conductivity of the gas in the second flame.

This converter 26 includes the converter material which, however, must be conveyed in correspondingly formed channels of the converter 26. This material may also have to be replaced during maintenance of the measurement devices, so that a good accessibility is desired.

As shown in FIG. 1, operating personnel can access the interior of the control cabinet 10 from an accessible frontal plane/side 28 that is spanned by the front side of the control cabinet 10. Two gas lines 30, 32 extend from the housing parts 20 to a connection housing part 22, in which an inlet channel 34 and an outlet channel 36 are formed, into each of which one of the gas lines leads. This connection housing part 22 is mounted with screws 41 on an assembly plate 40 which serves as a mounting plane 38, wherein the assembly plate 40 extends perpendicular to a rear wall 42 of the control cabinet 10 and is correspondingly arranged perpendicular to the accessible frontal plane/side 28 of the control cabinet 10.

Figure 2:
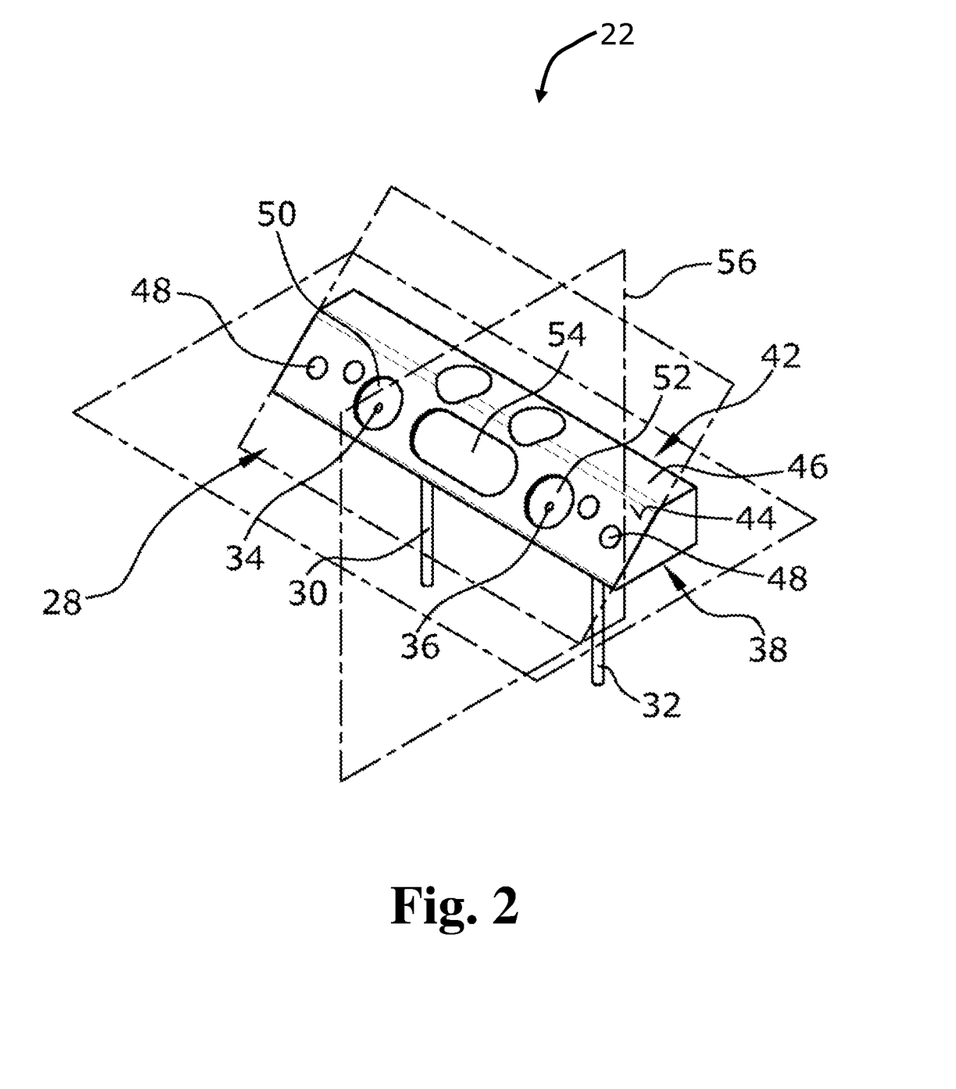
FIG. 2 shows a perspective view of a connection housing part of the analysis unit according to the present invention in FIG. 1.

The connection housing part 22 shown in FIG. 2 comprises a connection plane 44 that is tilted relative to the mounting plane 38 by 45° in the direction of the frontal plane/side 28, wherein the connection plane 44 merges into a contact face 46 in the area facing the rear wall 42, wherein the contact face 46 extends parallel to the mounting plane 38. The connection plane 44 of the connection housing part 22 is equipped with two threaded holes 48 in the outer area and a first circular recess 50 into which the inlet channel 34 leads, and is equipped with a second circular recess 52 from which the outlet channel 36 extends through the connection housing part 22, and is equipped with an oblong recess 54 in-between. The connection housing part 22 and the therein formed channels 34, 36, threaded holes 48 and recesses 50, 52, 54 are each arranged symmetrically to a symmetry plane 56, which runs perpendicular to the mounting plane 38 and the connection plane 44 and divides the connection housing part 22 centrally into two sections having the same size.

Figure 3:
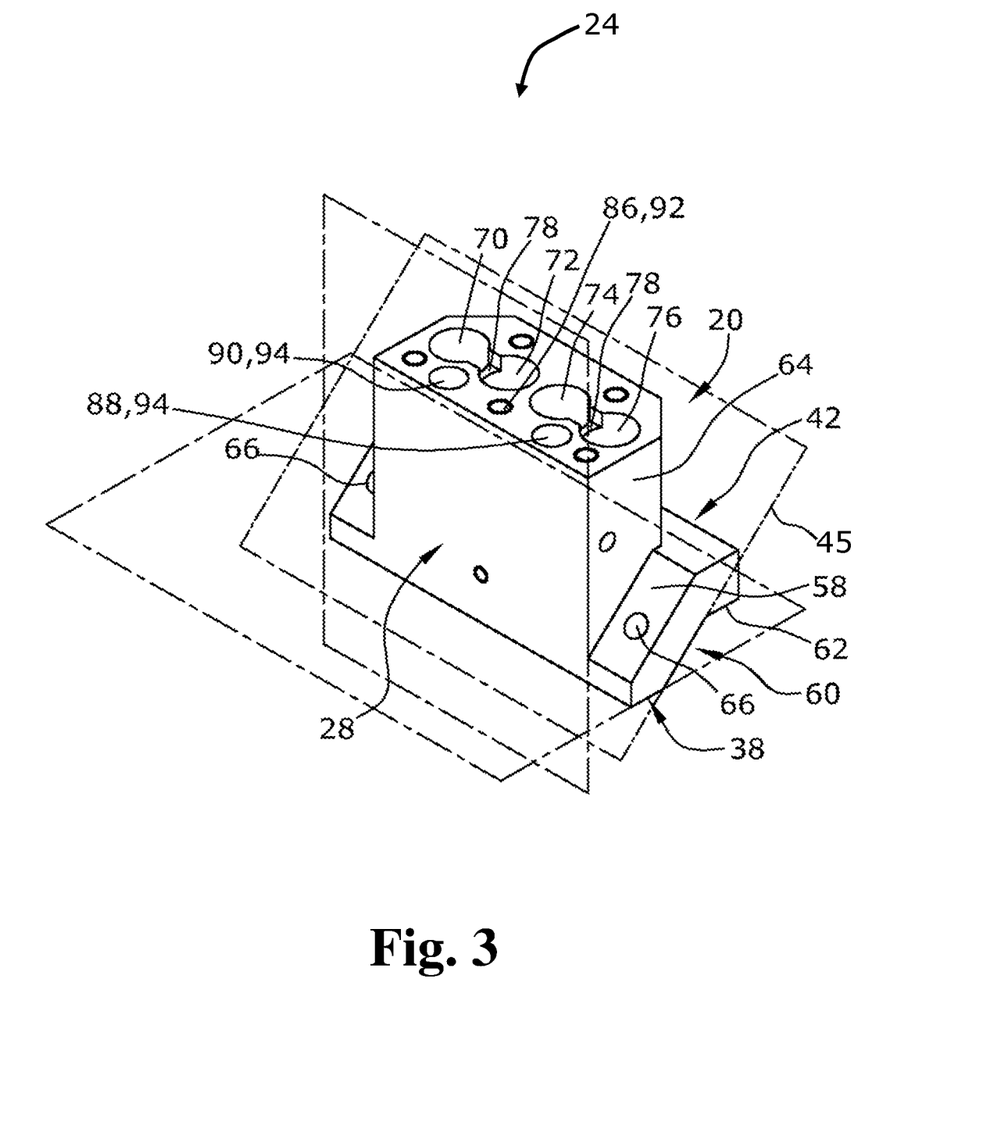
FIG. 3 shows a perspective view of a main housing part of the analysis unit according to the present invention in FIG. 1.
Figure 4:
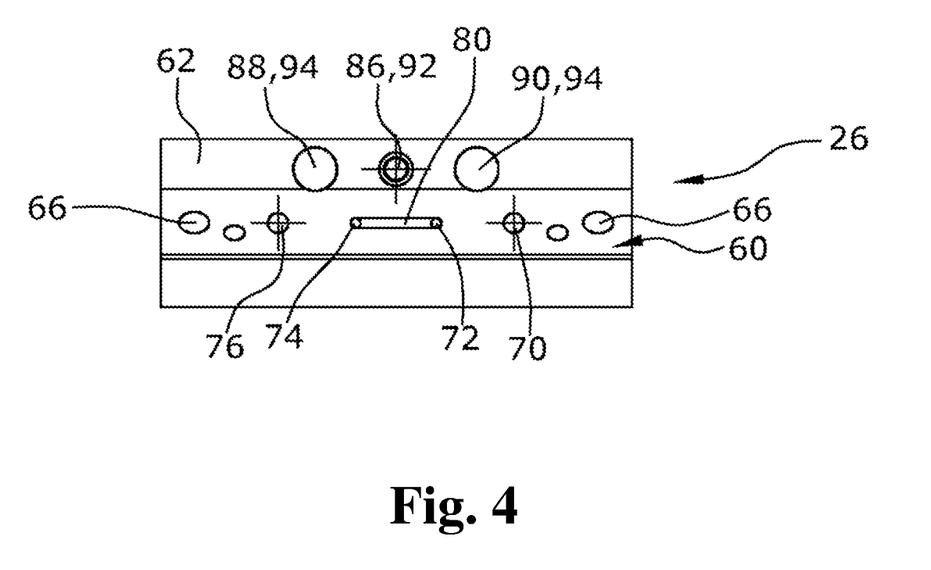
FIG. 4 shows a top view on the main housing part of the analysis unit according to the present invention in FIG. 1 from below.

A main housing part 24 of the converter 26 is mounted on the connection housing part 22, as is shown in FIGS. 3 and 4. The main housing part 24 comprises a flange plate 58 whose flange face 60, facing relative to the connection housing part 22, comprises a connection plane 45 after installation that corresponds to the connection plane 44 of the connection housing part 22. This flange face 60 merges into a face 62, which in turn is supported by the contact face 46 of the connection housing part 22 and correspondingly also extends parallel to the mounting plane 38, so that the main housing part 24 can be placed on the connection housing part 22 during installation since a body 64 of the converter 26 extends upwards from the flange plate 58 at an angle of 45°, i.e., it extends perpendicular to the mounting plane 38. In the flange plate 58, a bore 66 is formed on the right and on the left side of the body 64, wherein the bore 66 extends perpendicular to the flange face 60 through the flange plate 58 to an opposite flange face, and wherein screws 68 and threaded holes 48 can be placed in the bores 66 when mounting the main housing part 24 on the connection housing part 22. It is clear that these screws 68 can not only be accessed easily from the frontal plane/side 28, but that there is also sufficient space for turning a wrench due to the inclined arrangement.

The main housing part 24 comprises four channels 70, 72, 74, 76 that are arranged parallel to each other, wherein a first channel is an inflow channel 70, which is in fluid communication via an axial first circular recess 50 with the inlet channel 34 of the connection housing part 22, wherein the two middle channels serve as flow channels 72, 74, and wherein the other outer channel serves as a recirculation channel 76, which is in turn in fluid communication via the axial second circular recess 52 with the outlet channel 36. The inflow channel 70 is connected to the adjacent flow channel 72 via the axial recess 78, and the recirculation channel 76 is connected to the adjacent flow channel 74, wherein the axial recesses are formed on the separation wall between the respective two channels 70, 72, 74, 76 at the ending of the body 64 facing away from the connection housing part 22. On the opposite ending of the body 64 facing to the connection housing part 22, a connection channel 80, which is arranged opposite to the oblong recesses 54 of the connection housing part, is formed between the two flow channels 72, 74. The axial ending of the body 64 is closed by a plate 82 which is fastened with screws 84 on the ending of the body 64 of the main housing part 24, and thus closes the channels 70, 72, 74, 76. The consequence is that when a gas enters the inlet channel 34 of the connection housing part 22, the gas flows into the inflow channel 70 in order to then flow in a meandering way through the two flow channels 72, 74 into the recirculation channel 76 and from there into the outlet channel 36. The aforementioned converter material for accelerating the reaction is already contained in all four channels 70, 72, 74, 76. A sufficient reaction path and sufficient converter material is thereby provided for a full conversion of the non-methane hydrocarbons.

FIGS. 3 and 4 show three additional receiving openings 86, 88, 90 extending parallel to the channels 70, 72, 74, 76 on the main housing part. The middle receiving opening arranged in the symmetry plane 56 comprises a temperature sensor 92, which can be, for example, a PTC element and is arranged between the two other receiving openings 88, 90, in which one heating cartridge 94 is respectively arranged, which creates a temperature of approximately 280° C. in the converter 26, which is the temperature for an optimum reaction. These channels are also closed by the plate 82.

In addition to the aforementioned good accessibility for the installation and removal the converter 26, the converter 26 is designed so that, if the available vertical installation space is too small, the converter can also be installed horizontally by rotating it by 180° around its symmetry axis, in comparison to the presented installation position, and by tilting it forward by 90° in direction to the frontal plane. The channels are arranged so that only the flow direction of the main housing part is changed in this case, with no other structural changes being required for the connection housing part or the main housing part. This results in an increased number of common parts to be produced, whereby costs can be reduced.

It should be clear that the scope of protection of the present invention is not limited to the described exemplary embodiment, but that the symmetrical formation with the inclined flange connection can also be used for other housings with multiple parts in order to create analysis units adapted to the installation space with an optimum accessibility for installation. Reference should also be had to the appended claims.

What is claimed is:

1. An analysis unit comprising:
a frontal plane from which the analysis unit is accessible;
mounting planes each of which are arranged parallel with each other and perpendicular to the frontal plane; and
a gas measurement device comprising,
at least one connection housing part, the at least one connection housing part comprising,
an inlet channel which is arranged to extend from one of the mounting planes to a first connection plane, and
an outlet channel which is arranged to extend from the first connection plane to the one of the mounting planes, and
a main housing part comprising a second connection plane which corresponds to the first connection plane of the at least one connection housing part, the main housing part being arranged to rest on the first connection plane of the at least one connection housing part, the main housing part further comprising,
an inflow channel which is arranged to be in a fluid communication with the inlet channel of the at least one connection housing part via the first connection plane, and
a recirculation channel which is arranged to be in a fluid communication with the outlet channel of the connection housing part via the first connection plane,
wherein,
the first connection plane and the second connection plane are each tilted at an angle of 45° from the one of the mounting planes in a direction of the frontal plane.

2. The analysis unit as recited in claim 1, wherein,
the at least one connection housing part further comprises bores, channels, and recesses, the channels comprising the inlet channel and the outlet channel,
the main housing part further comprises bores, channels, and receiving openings, and all bores, channels, and recesses in the at least one connection housing part, and all bores, channels and receiving openings in the main housing part are arranged symmetrically relative to a symmetry plane which runs perpendicular to the one of the mounting planes.

3. The analysis unit as recited in claim 2, wherein,
the main housing part further comprises a flange plate which comprises a first flange face which forms the first connection plane and a second flange face which runs parallel to the one of the mounting planes, and
the bores of the main housing part extend perpendicular to the first flange face through the flange plate to an opposite flange face.

4. The analysis unit as recited in claim 3, further comprising:
screws,
wherein,
the bores of the at least one connection housing part are provided as two threaded holes which are configured so that the screws can be tightened therein, and
the screws are configured extend through the bores of the flange plate into the threaded holes.

5. The analysis unit as recited in claim 4, wherein,
the main housing part further comprises a body which is configured to extend between two of the bores at an angle of 45° relative to the first flange face and the second flange face, and
the main housing part is configured to be mountable in two perpendicularly arranged positions on the at least one connection housing part.

6. The analysis unit as recited in claim 1, wherein the first connection plane of the at least one connection housing part merges into a contact face which is arranged parallel to the one of the mounting planes.

7. The analysis unit as recited in claim 6, wherein the second connection plane of the main housing part merges into a face which is angled by 45° relative to the second connection plane and is arrangeable on the contact face of the at least one connection housing part in a first mounting position.

8. The analysis unit as recited in claim 1, wherein at least one of the inflow channel and the recirculation channel of the main housing part comprises a converter material which converts hydrocarbon into methane.

9. The analysis unit as recited in claim 8, wherein,
the main housing part further comprises a first flow channel and a second flow channel which are respectively arranged between the inflow channel and the recirculation channel, the first flow channel and the second flow channel being arranged parallel with respect to each other and being configured to have the converter material be arranged therein,
the first flow channel is connected to the inflow channel via a first axial recess, the first axial recess being arranged between an ending of the inflow channel facing away from the connection housing part and the first flow channel, and
the second flow channel is connected with the recirculation channel via a second axial recess, the second axial recess being arranged between the ending of the recirculation channel facing away from the connection housing part and the second flow channel.

10. The analysis unit as recited in claim 9, wherein the main housing part further comprises a connection channel formed at an ending facing to the at least one connection housing part between the first flow channel and the second flow channel, the connection channel being arranged to meander through the main housing part.

11. The analysis unit as recited in claim 10, wherein the first connection plane of the at least one connection housing part comprises,
- a first circular recess into which the inlet channel leads and which is in a fluid communication with the inflow channel of the main housing part,
- a second circular recess into which the recirculation channel of the main housing part leads and which is in a fluid communication with the outlet channel of the at least one connection housing part, and
- an oblong recess into which the first flow channel and the second flow channel of the main housing part lead.

12. The analysis unit as recited in claim 9, further comprising:
- a plate,
- wherein,
- the inflow channel, the recirculation channel, the first flow channel, and the second flow channel are each closed via the plate when the plate is screwed on their respective endings opposite to the connection housing part.

13. The analysis unit as recited in claim 1, wherein the main housing part further comprises,
- at least one first receiving opening in which a heating cartridge is arranged, and
- at least one second receiving opening in which a temperature sensor is arranged.

14. The analysis unit as recited in claim 1, wherein,
- the gas measurement device is a flame ionization detector, and
- the main housing part forms a converter.

* * * * *